United States Patent
Chiang et al.

[11] Patent Number: 5,478,894
[45] Date of Patent: Dec. 26, 1995

[54] PROCESS FOR PREPARING CROSSLINKED WATER ABSORBENT RESINS

[75] Inventors: William G. Chiang, Virginia Beach; Joy L. McCrickard, Portsmouth, both of Va.

[73] Assignee: Hoechst Celanese Corporation, Somerville, N.J.

[21] Appl. No.: 86,966

[22] Filed: Jul. 2, 1993

Related U.S. Application Data

[63] Continuation of Ser. No. 895,286, Jun. 8, 1992, abandoned.
[51] Int. Cl.⁶ ................. C08F 8/42; C08F 8/08
[52] U.S. Cl. .......... 525/369; 525/327.3; 525/378; 525/379
[58] Field of Search ............... 525/369, 368, 525/378, 379

[56] References Cited

U.S. PATENT DOCUMENTS

| | | | |
|---|---|---|---|
| 2,556,075 | 6/1951 | Erickson | 526/273 |
| 3,891,695 | 6/1975 | Ray-Chaudhuri | |
| 4,016,133 | 4/1977 | Hyosu et al. | |

FOREIGN PATENT DOCUMENTS 149910  9/1983  Japan .
759863  10/1956  United Kingdom .
9007528  7/1990  WIPO ................. C08F 220/28

*Primary Examiner*—Christopher Henderson
*Attorney, Agent, or Firm*—Hugh C. Crall

[57] ABSTRACT

This invention is directed to a recurring polymeric moiety of the following formula:

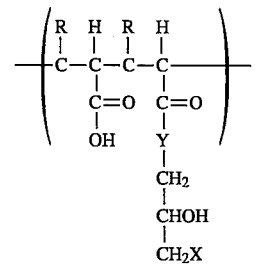

wherein R is independently selected from hydrogen and $C_1$ to $C_4$ alkyl; Y is independently selected from O and NH; and X is independently selected from Cl, F, Br, I, $NO_3$, $HSO_4$ and $H_2PO_4$.

Polymers of the above structure may be crosslinked by treating the polymer with a base and heating it.

7 Claims, No Drawings

PROCESS FOR PREPARING CROSSLINKED WATER ABSORBENT RESINS

This is a continuation of application Ser. No. 07/895,286 filed on Jun. 8, 1992 now abandoned.

BACKGROUND OF THE INVENTION

1. Technical Field

This invention relates specifically to fluid absorbent polymers known as super-absorbent polymers or hydrogel forming polymer compositions. However, the invention can be used to produce novel crosslinked polymer by a novel method. Such polymers are capable of absorbing large quantities of aqueous fluids and find many applications such as absorbents in diapers to their use as thickeners in cosmetics.

2. Prior Art Background

Super-absorbent polymers are well known. They comprise a group of essentially water-insoluble, partially crosslinked hydrogel forming polymer compositions which possess the ability to absorb large quantities of aqueous fluids. Examples of such super-absorbent polymers include crosslinked homopolymers, copolymers and graft polymers of a monomer having a carboxyl group or a monomer which can be polymerized and subsequently hydrolyzed to provide carboxyl moieties in the polymer chain. Specific examples of such super-absorbent polymer include partially crosslinked polyacrylic acid polymers, polymethacrylic acid polymers, starch or polyvinyl alcohol grafted acrylic or methacrylic acid polymers and hydrolyzates of starch grafted polyacrylonitrite polymers. Specific prior art patents disclosing super-absorbent polymers include: U.S. Pat. No. 4,654,039—a crosslinked, partially neutralized polyacrylic acid polymer; U.S. Pat. No. 4,076,663—a crosslinked, partially neutralized, starch grafted polyacrylic acid polymer; U.S. Pat. No. 4,389,513—a crosslinked, partially neutralized copolymer of isobutylene and maleic anhydride; U.S. Pat. No. 4,124,748—a crosslinked, partially neutralized saponification product of a vinyl acetate/acrylic acid copolymer; and U.S. Pat. No. 3,935,099 saponified starch-polyacrylonitrile graft copolymer.

Super-absorbent polymers are generally prepared by solution and inverse emulsion/suspension polymerization processes. U.S. Pat. Nos. 4,076,663 and 4,654,039 describe well known solution polymerization methods. U.S. Pat. Nos. 4,304,706 and 4,507,438 are examples of descriptions of the well known inverse suspension emulsion polymerization procedures. The teachings of these prior art patents are hereby incorporated by reference.

Super-absorbent polymers are essentially water insoluble due to the degree of crosslinking present in the polymer. However, the degree of crosslinking not only controls water solubility but also the amount and rate of water absorption, the processability of the polymer in the manufacturing process and other performance and processability properties of the polymer. This invention is directed to an advantageous method of crosslinking super-absorbent polymers and a process for preparing said super-absorbent polymers.

Crosslinking of the polymer is normally achieved in two ways. Internal crosslinkers can be added to the polymerization reaction mixture prior to polymerization and polymerization and crosslinking effected simultaneously. Alternately, the crosslinker is added to the reaction product after polymerization has been effected and the polymer is then crosslinked, Prepolymerization addition of the crosslinker has the advantage of greater crosslinking uniformity in the polymer. However, the pre-addition method results in a higher viscosity reaction product which can result in decreased productivity, higher equipment costs and increased process energy requirements. Post-addition results in less uniformity of crosslinking in the polymer reaction product and high energy cost because it is necessary to mix the crosslinker into a viscous reaction product.

It is the object of this invention to avoid the foregoing problems and provide an improved process for preparing super-absorbent polymer compositions.

SUMMARY OF THE INVENTION

This invention is directed to a method of introducing cross-linking into a super-absorbent polymer composition and composition of said method. The process comprises polymerizing from about 50 to 99.99 mole percent of ethylenically unsaturated monomer having at least one hydrophilic carboxyl group in the presence of a second monomer having one polymerizable ethylenically unsaturated group and a second group "Z" of the formula: —Y—CH$_2$—CHOH—CH$_2$X wherein Y is oxygen or amino and X is an anion of a strong acid. After polymerization of the reaction mixture has been completed, the group Z is converted to an epoxy group and the composition is heated to crosslink the polymeric chains. Optionally, a second crosslinker may be incorporated in the monomer mixture to induce crosslinking during polymerization. The process is also suitable for imparting crosslinking into water soluble polymers having carboxyl moieties in the polymeric chain.

DESCRIPTION OF THE PREFERRED EMBODIMENTS

The super-absorbent polymer composition of this invention are made by polymerizing from about 10 to 99.99, preferably about 50 to 99.99, most preferably about 70 to 99 weight percent of an ethylenically unsaturated monomer having at least one hydrophilic carboxyl group in the presence of second ethylenically unsaturated hydrin monomer of the formula:

where:

R is H, or C$_1$–C$_4$ alkyl

Y is O or NH

X is CL, F, BR, I, NO$_3$, HSO$_4$, and H$_2$PO$_4$.

The polymerization is conducted under free radical polymerization conditions using from about 0 to 5 mole percent of a free radical initiator based upon the weight of monomer and about 0.01 to about 15 weight percent of said hydrin monomer; preferably about 0.1 to about 10 weight percent and most preferably about 0.5 to about 5 weight percent.

The invention may be illustrated by the following reaction scheme wherein R and Y are defined above and X is chlorine.

I. Chlorohydrin Ester and Amide Synthesis

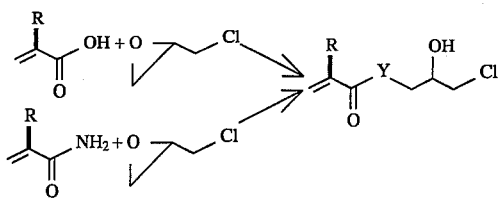

Hydrin monomers may be prepared by the general procedures described in the following literature references:

"The Reaction Of Methacrylic Acid With Epichlorohydrin Upon Catalysis With Tertiary Amines", UKRAINSKII KHIMICHESKII ZHURNAL, Vol. 50 No. 1, pp 92–97, 1984. "Kinetics And Mechanism Of Auto Catalytic Reaction Of Acrylic Acid With Epichlorohydrin In Presence Of Basic Catalysts", Polish Journal of Chemistry, Vol. 55, pp 1595–1605, 1981.

II. Crosslinked Polymer Synthesis

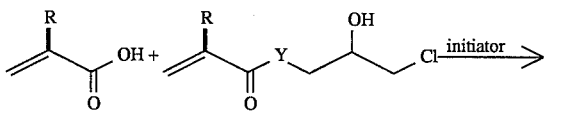

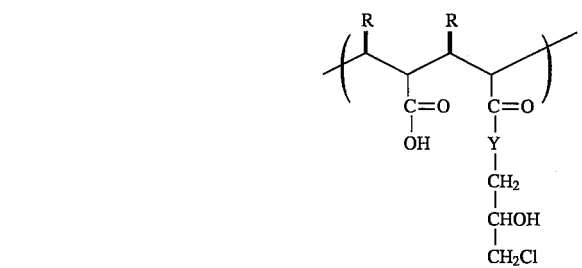

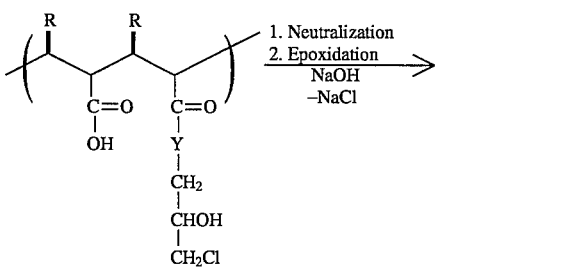

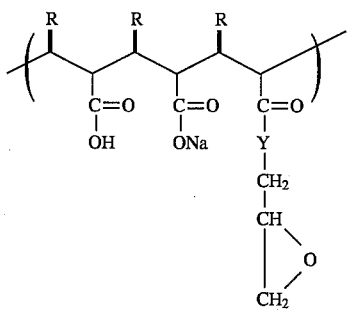

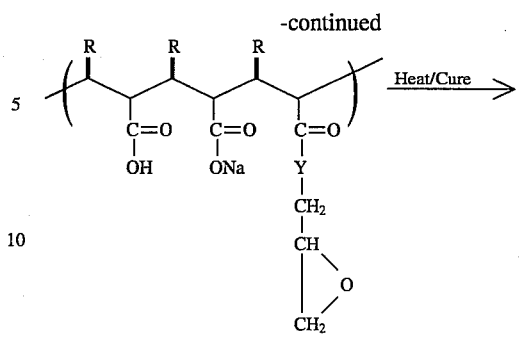

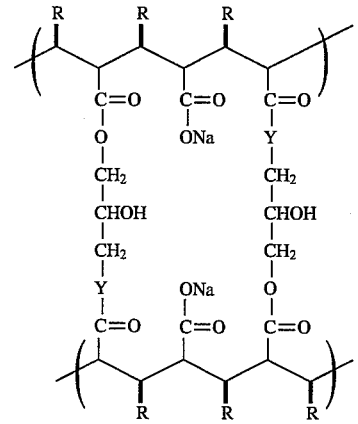

This invention is a novel method of preparing a crosslinked polymer which comprises polymerizing a first ethylenically unsaturated monomer having one polymerizable unsaturated bond and at least one carboxyl group in the presence of a substituted hydrin monomer having one polymerizable unsaturated bond to form a copolymer of said first ethylenically unsaturated monomer and said hydrin monomer. The copolymer of said first ethylenically unsaturated monomer and hydrin monomer is contacted with a base to neutralize between 25 to 90 mole percent of the carboxyl groups and to convert substituted hydrin moiety to an epoxy moiety or epoxy group. The polymer is then heated to crosslink it.

The super-absorbent polymers may be prepared by the invention using the general methods disclosed in U.S. Pat. No. 4,076,663 to Masuda et al and U.S. Pat. No. 4,654,039 to Brandt et. al.; the teachings of which are incorporated by reference.

Optionally, the polymerization may be conducted in the presence of a second crosslinker in an amount up to about 0.001 to 1.0 mole percent based upon polymerizable monomer; preferably about 0.005 to about 0.3 mole percent. Another optional component in the polymerization mixture may include water soluble hydroxy containing components such as water soluble polysaccharides such as starch, water soluble celluloses, and polyvinyl alcohols. These graftable polymers may be used in an amount up to about 15 weight percent based upon ethylenically unsaturated monomer.

The preferred ethylenically unsaturated carboxyl monomers useful in the invention are acrylic and methacrylic acid. Other useful monomers include chloro-substituted acrylic and methacrylic acid, maleic acid, fumaric acid, maleic anhydride etc; acrylic acid is most preferred. These monomers may be partially neutralized prior to polymerization provided that no more than 50 mole percent of the carboxyl groups are neutralized prior to polymerization.

The ethylenically unsaturated carboxyl monomers useful in the invention may be copolymerized with other non-carboxyl monomers such as those disclosed in U.S. Pat. No. 4,076,663 to Masuda. Specific examples of such monomers include styrene, methyl acrylate, ethyl acrylate, vinyl acetate etc; preferably the resulting polymer is made from at least about 50 mole percent carboxyl containing monomer in the free acid form.

The polymerization reaction may be conducted under solely thermal polymerization conditions. However, preferably a free radical initiator is used. Exemplary initiators are the water soluble persulfate salts of potassium, sodium and ammonium, hydrogen peroxide, benzoyl peroxide, lauryl peroxide, t-butyl perbenzoate, azobis-isobutyronitrile etc. Free radical initiation may be effected using a redox initiator system comprising an oxidizing agent and a reducing agent. Suitable oxidizing agents are hydrogen peroxide, the alkali metal persulfates, ammonium persulfate, diacryl peroxides, peresters, and alkyl hydroperoxides. Suitable reducing agents are alkali metal sulfites, alkali metal bisulfites, ferrous salts, ascorbic acid, etc. Preferably a dual catalyst initiator system is employed consisting of a redox initiator system and a thermal peroxy, perester or azo free radical initiator; e.g. a redox system comprising ascorbic acid and hydrogen peroxide and a thermal free radical initiator such as 2,2'-azobis isobutyronitrile.

The thermal free radical initiators may be used in an amount of up to about 2 mole percent based upon ethylenically unsaturated monomer preferably from about $1 \times 10^{-4}$ to 1.0 mole percent. In the case of a redox system, the reducing agent may be present in an amount of about $6 \times 10^{-5}$ to $2.5 \times 10^{-2}$ mole percent based upon ethylenically unsaturated monomer; preferably $6 \times 10^{-4}$ to $2.5 \times 10^{-3}$ mole percent. The amount of oxidizing agent used is from about $1 \times 10^{-4}$ to 1 mole percent, preferably $3 \times 10^{-3}$ to 0.5 mole percent, most preferably about 0.15 to about 0.3 mole percent based upon monomer.

Thermal initiators of the peroxy, perester, azo types may be used to initiate polymerization in an amount up to 2 mole percent preferably up to about 1 mole percent and most preferably up to about 0.5 mole percent. However, preferably the redox initiator system is used to initiate and polymerize the bulk of the polymerizable monomer and a thermal initiator is used to reduce the residual monomer to below 1000 PPM. Useful thermal initiators must have sufficient solubility in the monomer reaction mixture and have at least a 10-hour half life at 30° C. Examples of preferred, useful azo initiators are 2,2'-azobis (amidino propane) dihydrochloride, 4,4'-azobis (cyanovaleric acid), 4,4'-butylazocyanovaleric acid, 2,2'-azobis isobutyronitrile, and the like. A most preferred azo initiator for use in this invention is 2,2'-azobis (amidinopropane) dihydrochloride. The thermal initiators are preferably used in the amount of about 0.1 to about 0.4 weight percent and most preferably, 0.25 to 0.35 weight percent, wherein said weight percents are based on the weight of monomer.

Optionally, an internal crosslinker may be added to the ethylenically unsaturated monomer prior to polymerization to internally crosslink the polymer. Internal crosslinking agents can be used in an amount of about 0.001 to 5 mole percent based upon polymerizable monomer and are selected from polyfunctional monomers having at least two reactive polymerizable groups, vinyl monomers having one reactive vinyl group and at least one functional group which is reactive with at least one of the monomers of the polymerization mixture and compounds containing at least two functional groups which are reactive with at least one of the polymerization monomers. Examples of internal crosslinkers include: tetraallyloxy ethane, N,N'-methylene bisacrylamide, N,N'-methylene bismethacrylamide trimethylol propane triacrylate, glycerol propoxy triacrylate, triallylamine, divinyl benzene divinyltoluene, polyethylene glycol monoallyl ether, glyoxal, ethylene glycol, di- or polyglycidyl ether and ethylene diamine.

The polymerization process may be conducted at a temperature from about 5° C. to about 100° C. The reaction time will vary depending upon the amount of initiator, the monomer concentration, the specific initiators. These parameters are well known to one skilled in the art.

The polymer should have at least 25 and more preferably about 50 mole percent and most preferably about 70 to 75% mole percent of its carboxyl group neutralized with a base such as ammonium, an alkali or an amine preferably a caustic alkali. Preferably the carboxyl groups are neutralized after polymerization. A preferred neutralizing agent is sodium hydroxide.

The invention may be carried out by the solution polymerization method which is described in detail in U.S. Pat. No. 4,076,663 to Masuda et al; the teachings of which are hereby incorporated by reference.

Also, the invention may be practiced using the inverse suspension polymerization method which is described in detail in U.S. Pat. No. 4,340,706 to Obayashi et al; the teachings of which are hereby incorporated by reference. The solution polymerization method is preferred.

The super-absorbent polymer of this invention is evaluated by the following tests:

1) Absorbency Under Pressure

This test determines the ability of a super-absorbent polymer to absorb under a pressure of 20 g/cm$^2$ (i.e., child sitting down).

Absorbency under Pressure can be measured using an Automatic Absorbency Tester, Model KM 350 (Kyowa Seiko Co., Ltd) and a plastic tube having an inner diameter of 28 mm and a length of 50 mm with a wire net (100 mesh) at the bottom of the tube. Samples having a mesh size of 32–100 are used in the test.

A test sample, 0.100±0.01 g., is placed in the plastic tube and is spread evenly over the wire net. A 100 g weight is placed on the sample. The plastic tube is placed at the center of the porous plate of the Tester under which is a reservoir containing saline solution (0.90 wt/vol. % NaCl aqueous solution). After 1 hour of absorption, the volume of absorbed saline solution is determined (a ml). A blank is run using the same procedure without the super-absorbent polymer (b ml). Absorbency under Pressure is equal to (a–b)×10.

2) Centrifuge Retention Capacity

This test is conducted using a Clay Adams Dynac II centrifuge available from Clay Adam, Parsipanny, N.J., a division of Becton-Dickinson & Co. The basket of the centrifuge was modified to accept the teabag test samples used herein. Test specimens were prepared (2½ by 3 inch "teabags") from "teabag paper" (heat sealable, 3 inch wide Kimberly-Clark grade 542).

A test superabsorbent polymer (SAP) sample of 0.200±0.005 grams of −30/+50 mesh particle size superabsorbent polymer on tared weighing paper. The weight of the empty "teabag" is recorded as Wt 0. The SAP sample is transferred into the weighed "teabag" and the open end is sealed. The sample plus teabag is weighed and this weight is recorded as Wt 1. The open ends of two empty "teabags" are sealed and used as blanks and their dry weights are recorded as Wb 0.

The sealed "teabags" are placed in a pan filled to 1.5 inch depth with 0.9% (wt/wt) saline. After 30 minutes, the "teabags" are removed and laid on a flat, nonabsorbent, surface. The "teabags" are transferred to the centrifuge and are centrifuged at 1600 rpm for 3 minutes. The centrifuge is stopped and the "teabags" are removed and weighed. This weight is recorded as Wt 2; record blank wet weights as Wb 2.

The centrifuge retention value is then calculated in accordance with the formula:

$$\frac{\text{Centrifuge Retention Capacity}}{\text{gram/gram}} = \frac{Wt\,2 - Wt\,1 - Wb\,2 + Wb\,0}{Wt\,1 - Wt\,0}$$

3) Shear Modulus

I. Sample Preparation 30 g of 0.9% saline is weighed into an aluminum pan. A stirring bar is added to the saline and it is placed on a magnetic stirrer. Stirring is effected to create a vortex and 1.0 g polymer is poured slowly into the stirring saline. The stir bar is removed when the vortex closes. The sample is covered with plastic wrap and allow to hydrate for one hour.

II. Testing

A controlled strain rheometer, manufactured by Rheometrics, Inc. of Piscataway, N.J., called a Rheometrics Fluid Spectrometer, Model 8400 (RFS-8400) is used to measure the shear modulus value of the polymers. The instrument is set to the following conditions:

| Mode: | strain sweep |
|---|---|
| Geometry: | parallel plate |
| Rate: | 100 hertz |
| Strain: | 01 + 0 |
| Offset: | 0 |
| Steady: | Dynamic |
| Plate Radius: | 25 mm |

The previously prepared sample is spread on paper towels and gently mixed with a wooden spatula to remove excess fluid. Fifteen grams of hydrated polymer is then placed in the Rheometrics cup which fits into the 25 mm bottom plate of the test device. The polymeric material is spread over the bottom surface of the cup. The top plate is lowered until a gap of 2.5 mm between plates is achieved. The test sequence is started and the RFS prints the modulus and strain values over the range selected. A plot of % strain versus storage modulus (G') is prepared and extrapolated to zero. The intercept at 0% strain is reported as the Shear Modulus value.

Preparation of 3-Chloro-2-hydroxypropyl Acrylate (CHPA)

EXAMPLE 1

Benzyltriethylammonium chloride (BTEAC) as a catalyst

To a 1000 mL. 3-necked round bottomed flask equipped with a thermometer, agitator and reflux condenser were charged 360.3 grams (5 moles) of acrylic acid, 462.65 grams (5 moles) of epichlorohydrin, 1.8 grams MEHQ as polymerization inhibitor and 11.39 grams (0.05 mole) of benzyltriethylammonium chloride as catalyst. The reaction mixture was heated to 80° C. for 4 to 5 hours.

The optimal conditions for the synthesis of CHPA with a yield of 95% recalculated to acrylic acid, were determined on the basis of the data; molar ratio of $C_{AA}/C_{EPI}=1:1$, reaction temperature 80° C., molar ratios of catalyst to acrylic acid were $C_{BTEAC}/C_{AA}=0.01:1$ or $C_{TEA}/C_{AA}=0.04:1$. The reaction is completed within 5 hours.

The composition of the CHPA reaction mass was investigated by the gas chromatographic method. An analytical curve which include nine components, epichlorohydrin (EPI), acrylic acid (AA), glycidylacrylate (GA), 1,3-dichloropropane (DCP), chloropropane-1,2-diol (CPD), 3-chloro-2-hydroxypropyl acrylate (CHPA), 3-chloro-1-hydroxypropyl acrylate (CHPA-isomer), p-methoxyphenol (MEHQ) and 2-hydroxypropane-1,3-diacrylate (HPDA), was prepared for qualitative and quantitative determination of the reaction mass. The concentration of standards ranged from 100 to 900 ppm. The results indicated the CHPA reaction mass has the following composition.

| COMPONENT | WEIGHT % |
|---|---|
| CHPA & ISOMER | 92 |
| EPI | 2 |
| AA | 1.5 |
| DCP | 2 |
| GA | 0.4 |
| HPDA | 1 |
| MEHQ | 0.2 |

Preparation of 3-Chloro-2-hydroxypropyl Methacrylate (CHPM)

EXAMPLE 2

Triethylamine (TEA) as a catalyst

To a 500 mL. 3-necked round bottomed flask equipped with a thermometer, air driven agitator and reflux condenser were charged 172.18 grams (2 moles) of methacrylic acid, 203.57 grams (2.2 moles) of epichlorohydrin, 0.86 grams (0.5 weight % of MAA) of MEHQ as polymerization inhibitor and 8.10 grams (0.08 mole) of triethylamine as catalyst. The reaction mixture was heated to 85° C. and a significant exotherm was observed when reaction temperature reaching 85° C. The reaction mixture was held at this temperature for another 4 hours. A clear pale yellow liquid is the final product and the yield was greater than 99% conversion based on methacrylic acid concentration.

Gas chromatographic analysis showed that the reaction mixture has the following composition.

| COMPONENT | WEIGHT % |
|---|---|
| CHPM & Isomer | 90.03 |
| EPI | 1.87 |
| MAA | 0.22 |
| DCP | 4.44 |
| GMA | 1.31 |
| MEHQ | 0.18 |
| HPDMA | 0.50 |

EXAMPLE 3

SAP synthesis with TAE as an internal crosslinker and no CHPA 2856.6 parts of deionized water were placed in a four necked, 4-liter reaction vessel equipped with a mechanical stirrer, nitrogen inlet, thermometer. 300 parts of 8% (0.14802 mole) oxidized starch in water, 3.4 parts (0.01321) of tetrallyloxy ethane in 800 parts (11.25873 mole) of glacial acrylic acid were transferred into reactor. The reaction mixture then cooled to around 10° C. and stirred vigorously. Nitrogen was purging through the reaction mixture and when the dissolved oxygen was reduced below 1 ppm, the following catalysts were added in the listed order: 8 parts of 10% (0.00294 mole) azo initiator 2,2-azobis (amidino propane) dihydrochloride in water; 24 parts (0.00014 mole) of 0.1% ascorbic acid in water; and 8 parts (0.02352 mole) of 10% hydrogen peroxide in water were added.

After a short induction period, polymerization began and a peak temperature of 60°–65° C. was reached within one hour. The gel was kept in an insulated container for 3.5 hours to reduce residual acrylic monomer to below 1000 ppm.

To the polymer gel after being chopped in a meat grinder were added 640 parts of 50% sodium hydroxide in water. The gel was again chopped to mix for uniform neutralization. The polymer was then dried to a moisture content of less than 5% on a rotary type drum dryer at 105° C. The resulting flake polymer was then ground and sieved to a particle size of 20–325 meshes.

The polymer exhibited the following properties:
Absorbency under pressure—10.7 gm/gm
Centrifuge Retention—39.7 gm/gm
Shear Modulus—36,250 dyne/cm$^2$

EXAMPLE 4

SAP synthesis with ethylene glycol diglycidyl ether as a post-reaction crosslinker 500 grams of the neutralized gel prepared as in Example 3 were then added 12.513 parts of 1% ethylene glycol diglycidyl ether in 32.04 parts of water. The gel was again chopped to obtain uniform distribution of the post crosslinking agent. The polymer was then dried to a moisture content of less·than 5% on a rotary type drum dryer at 105° C. The resulting flake polymer was then ground and sieved to a particle size of 20–325 mesh.

The polymer exhibited the following properties:
Absorbency under pressure—28.8 gm/gm
Centrifuge Retention—28.9 gm/gm
Shear Modulus—39,000 dyne/cm$^2$

EXAMPLE 5

SAP synthesis with 0.01215 mole of CHPA as a comonomer

A polymerization was carried out using the amounts of materials and methods of Example 3, except that additional 2.1 parts (0.01215 mole) of 95% of 3-chloro-2-hydroxypropyl acrylate (CHPA); 0.25% by weight based on concentration of the acrylic acid; was transferred into reactor with acrylic acid and starch.

The polymer exhibited the following properties:
Absorbency under pressure—23.1 gm/gm
Centrifuge Retention—29.6gm/gm
Shear Modulus—35,000 dyne/cm$^2$

EXAMPLE 6

SAP synthesis with 0.0243 mole of CHPA as a comonomer

A polymerization was carried out using the amounts of materials and methods of Example 3, except that 4.2 parts (0.0243 mole) of 95% of 3-chloro- 2-hydroxypropyl acrylate (CHPA); 0.5% by weight based on concentration of the acrylic acid; was transferred into reactor.

The polymer exhibited the following properties:
Absorbency under pressure—27.5 gm/gm
Centrifuge Retention—25.8 gm/gm
Shear Modulus—41,650 dyne/cm$^2$

EXAMPLE 7

SAP synthesis with 0.04861 mole CHPA as a comonomer

A polymerization was carded out using the amounts of materials and methods of Example 3, except that 8.4 parts (0.04861 mole) of 95% of 3-chloro- 2-hydroxypropyl acrylate (CHPA); 1.0% by weight based on concentration of the acrylic acid; was transferred into reactor.

The polymer exhibited the following properties:
Absorbency under pressure—25.0 gm/gm
Centrifuge Retention—22.6 gm/gm
Shear Modulus—44,000 dyne/cm$^2$

EXAMPLE 8

SAP synthesis with 0.07291 mole of CHPA as a comonomer

A polymerization was carried out using the amounts of materials and methods of Example 3, except that 12.6 parts (0.07291 mole) of 95% of 3-chloro- 2-hydroxypropyl acrylate (CHPA); 1.5% by weight based on concentration of the acrylic acid; was transferred into the reactor.

The polymer exhibited the following properties:
Absorbency under pressure—24.1 gm/gm
Centrifuge Retention—20.2 gm/gm
Shear Modulus—47,000 dyne/cm$^2$

EXAMPLE 9

SAP synthesis with no internal crosslinker 2860 parts of deionized water were placed in a four necked, 4-liter reaction vessel equipped with a mechanical stirrer, nitrogen inlet, thermometer. 300 parts (0. 14802 mole) of 8% oxidized starch in water 1.363 parts (0.00786 mole) of 95% CHPA in 800 parts of glacial acrylic acid were transferred into reactor. The reaction mixture then cooled to around 10° C. and stirred vigorously. Nitrogen was purging through the reaction mixture and when the dissolved oxygen was reduced below 1 ppm, the following catalysts were added in the listed order: 8 parts (0.02352 mole) of 10% azo initiator 2,2-azobis (amidino propane) dihydrochloride in water; 20 parts (0.00011 mole) of 0.1% ascorbic acid in water; and 8 parts (0.02352 mole) of 10% hydrogen peroxide in water were added.

After a short induction period, polymerization began and a peak temperature of 60°–65° C. was reached within one hour. The gel was kept in an insulated container for 3.5 hours to reduce residual acrylic monomer to below 1000 ppm.

To the polymer gel after being chopped in a meat grinder were added 640 parts of 50% sodium hydroxide in water. The gel was again chopped to mix for uniform neutralization. The polymer was then dried to a moisture content of less than 5% on a rotary type drum gryer at 105° C. The resulting flake polymer was then ground and sieved to a particle size of 20–325 meshes.

The polymer exhibited the following properties:
Absorbency under pressure—8.2 gm/gm
Centrifuge Retention—37.6 gm/gm

EXAMPLE 10

SAP Synthesis with 0.016 mole of CHPA

A polymerization was carried out using the amounts of materials and method of Example 9, except that 2.73 parts (0.01573 mole) of 95% of 3-chloro- 2-hydroxypropyl acrylate (CHPA); 0.32% by weight based on concentration of the acrylic acid; was transferred into the reactor.

The polymer exhibited the following properties:
Absorbency under pressure—11.2 gm/gm
Centrifuge Retention—27.0 gm/gm

EXAMPLE 11

SAP Synthesis with 0.031 mole of CHPA

A polymerization was carried out using the amounts of materials and methods of Example 9, except that 5.45 parts (0.03146 mole) of 95% of 3-chloro- 2-hydroxypropyl acrylate (CHPA); 0.65% by weight based on concentration of the acrylic acid; was transferred into the reactor.

The polymer exhibited the following properties:
Absorbency under pressure—20.6 gm/gm
Centrifuge Retention—23.7 gm/gm

We claim:

1. A method of preparing a water-insoluble, partially cross-linked, hydrogel-forming polymer which comprises:

(a) polymerizing a first ethylenically unsaturated water soluble monomer having at least one hydrophilic carboxy group in the presence of a second ethylenically unsaturated monomer of the formula:

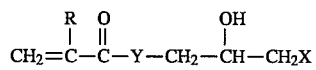

wherein:
   said first ethylenically tinsaturated water soluble monomer is present in an mount of at least 50% by weight;
   R is independently selected from H and $C_1$ to $C_4$ alkyl;
   Y is independently selected from O and NH; and
   X is independently selected from Cl, Br, F, I, $NO_3$, $HSO_4$ and $H_2PO_4$;

(b) contacting the polymerization product of step (a) with a base to convert the terminal portion of said second monomer to an epoxy group; and (c) heating said polymerization product to effect crosslinking of said polymerization product.

2. A method according to claim 1 wherein R is independently selected from H and $CH_3$.

3. A method according to claim 2 wherein Y is independently selected from O and NH and X is Cl.

4. A method according to claim 3 wherein Y is O.

5. A method according to claim 4 wherein said first ethylenically unsaturated monomer is present in an amount of at least 50 percent by weight.

6. A method according to claim 5 wherein said first ethylenically unsaturated monomer is independently selected from acrylic acid, methacrylic acid and the water soluble salts thereof.

7. A method according to claim 6 wherein said base is sodium hydroxide.

* * * * *